United States Patent [19]

Kiely et al.

[11] Patent Number: 4,945,160

[45] Date of Patent: Jul. 31, 1990

[54] PREPARATION OF CERTAIN 7-SUBSTITUTED QUINOLONES

[75] Inventors: John S. Kiely, Ann Arbor, Mich.; Lawrence E. Lesheski, Dublin, Ohio; Mel C. Schroeder, Dexter, Mich.

[73] Assignee: Warner-Lambert Company, Morris Plains, N.J.

[21] Appl. No.: 275,149

[22] Filed: Nov. 22, 1988

[51] Int. Cl.$^5$ .............................................. C07D 215/56
[52] U.S. Cl. .................................... 540/481; 540/597; 546/14; 546/156
[58] Field of Search ................ 540/481, 597; 546/123, 546/156, 14

[56] References Cited

U.S. PATENT DOCUMENTS 4,623,650 11/1986 Gilligan et al. ..................... 546/156
4,665,079 5/1987 Culbertson et al. ................ 546/123

OTHER PUBLICATIONS

Echevarren et al., J.A.C.S., vol. 109, pp. 5478–5486, (1987).

Primary Examiner—John M. Ford
Assistant Examiner—Bernard Dentz
Attorney, Agent, or Firm—Elizabeth M. Anderson

[57] ABSTRACT

Novel processes for the coupling of alkyl, alkenyl, alkynyl, or aryl groups to the seven position of quinolines and naphthyridines is disclosed. Novel intermediates and final compounds having antibacterial activity are also described as well as the formulations for the same use.

10 Claims, No Drawings

PREPARATION OF CERTAIN 7-SUBSTITUTED QUINOLONES

BACKGROUND OF THE INVENTION

· A palladium-catalyzed coupling reaction of aryl triflates with organostannanes in the presence of lithium chloride is disclosed in *J. Am. Chem. Soc.* 1988, 109, 5478–5486.

U.S. Pat. No. 4,665,079 discloses certain quinolones and naphthyridines substituted at the seven position by

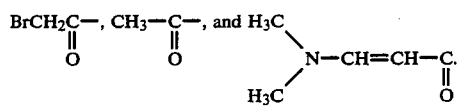

U.S. Pat. No. 4,623,650 discloses certain 7-aryl quinolones.

SUMMARY OF THE INVENTION

The instant invention is a process for the preparation of a compound of formula

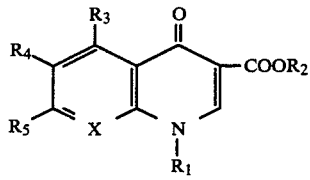

or a pharmaceutically acceptable salt thereof wherein $R_1$, $R_2$, $R_3$, $R_4$, $R_5$, and X are as described below.

The instant invention covers certain novel intermediates and novel compounds as described hereinbelow.

The instant invention covers a pharmaceutical composition of the novel compounds together with a pharmaceutically acceptable carrier. The invention also covers a method of treating bacterial infections in mammals which comprises administering the above pharmaceutical composition.

DETAILED DESCRIPTION

The instant invention is a process for the preparation of a compound of formula

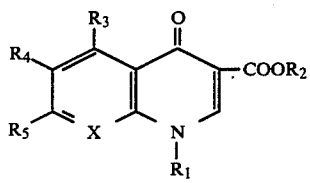

or a pharmaceutically acceptable salt thereof wherein
$R_1$ is lower alkyl, aryl, alkenyl, cycloalkyl of from three to six carbon atoms,
$R_2$ is hydrogen, alkyl, or metal salts;
$R_3$ is hydrogen, halogen, $OR_8$, alkyl, $N(R_9)_2$
  wherein $R_8$ is hydrogen, lower alkyl, lower acyl, trialkylsilyl
  and $R_9$ is hydrogen, lower alkyl, lower acyl maleimido, phthalimido, succinimido;
$R_4$ is hydrogen, halogen or lower alkyl;
X is N or $CR_{10}$ wherein $R_{10}$ is hydrogen, halogen, CN, $CF_3$, $OR_8$, alkyl, $N(R_9)_2$ wherein $R_8$ and $R_9$ are as above;
X and $R_1$ may be joined by $C-Y-CH_2CH(CH_3)$ where Y is O, S or N-alkyl to form a ring;
$R_5$ is alkyl, aryl, alkenyl, cycloalkyl, or cycloalkenyl,

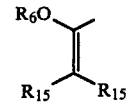

wherein $R_6$ is lower alkyl or $R_7Si$
wherein $R_7$ is lower alkyl or phenyl
and $R_{15}$ is hydrogen, alkyl, alkenyl, aryl, or halogen;
or $R_5$ may be a saturated or partially unsaturated heterocyclic ring such as but not limited to

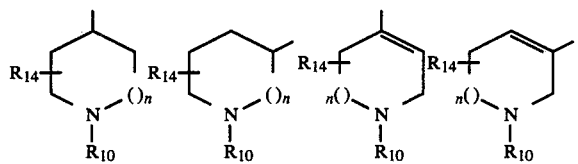

wherein n is an integer of from 0 to 4 and when a structure contains multiple n's it is not necessary that they be the same integer, but they may be, and $R_{10}$ is hydrogen, lower alkyl, or lower acyl and R– is one or more substituents selected from H, alkyl, aryl, or halogen provided the ring is attached through a carbon atom of the heterocyclic ring,
or $R_5$ is

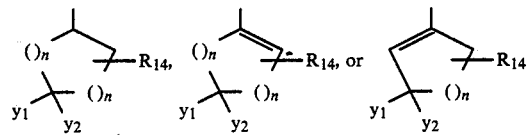

wherein $Y_1$ and $Y_2$ are each independently hydrogen, alkyl, $OR_8$ or
$N(R_9)_2$ or taken together are =O or =$NOR_8$ wherein $R_8$ and $R_9$ are as above; and n=0–4, as above, and $R_{14}$ is as above;
which comprises reacting a compound of formula

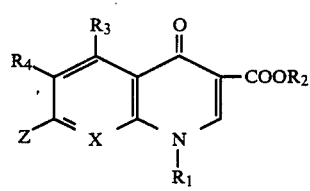

or a pharmaceutically acceptable salt thereof wherein $R_1$, $R_2$, $R_4$, and X are as described above and
Z is halogen when the compound is a naphthyridine and
Z is (halogen)$_3CSO_3$— when the compound is a quinolone with a tetraorganostannane of the formula III $(R_{12})_3SnR_{13}$ wherein $R_{12}$ is alkyl, alkenyl, alkynyl, cycloalkyl, cycloalkenyl, aryl, and $R_{13}$ is alkyl or

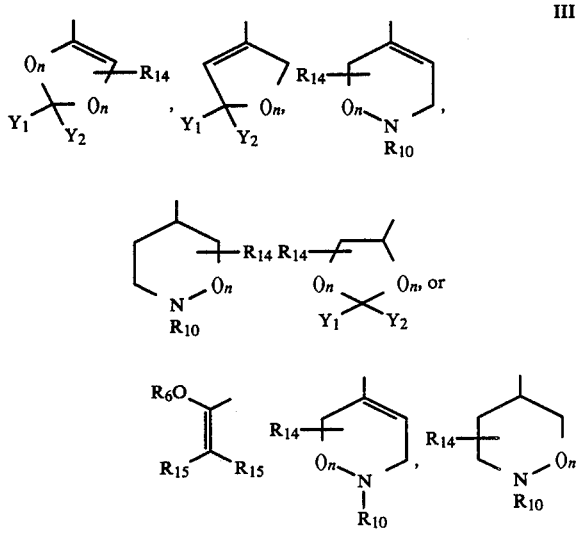

wherein n, $R_{14}$, $R_{10}$, $R_6$, $R_{15}$, $Y_1$ and $Y_2$ are as described previously to produce the desired compound of formula I.

The reaction takes place in a variety of convenient solvents such as ether, tetrahydrofuran, 1,2-dialkoxyethanes, dimethylformamide, or dioxane. Preferred solvents are tetrahydrofuran, dimethylformamide, and dioxane.

The reaction is catalyzed or promoted in a stoichometric fashion by a Pd(II) or Pd(0) compound such as bis(triphenylphosphine)palladium$^{II}$ chloride, tetrakis(triphenylphosphine)palladium(0), and other like palladium catalysts.

An anhydrous metal chloride is added to the reaction vessel when the process involves a quinolone compound. Preferred are lithium, sodium, cesium chlorides. Especially preferred is lithium chloride.

For improved yields, a phenolic antioxidant such as butylated hydroxy toluene or 2,6-di-(tertbutyl)-4-methylphenol is added to the reaction vessel.

The reaction takes place at temperatures of from about 30° to about 200° C. Preferred reaction temperature is from about 55° to about 110° C. The most preferred reaction temperature is from about 65° to about 105° C. Higher temperatures usually require shorter reaction times.

The reaction time may vary from about one hour to about three days. Preferably the reaction time is about 3 to 24 hours.

Preferred intermediates in the above process include but are not limited to:
1-(1,1-dimethylethoxycarbonyl)-4-hydroxy-4-(tributylstannyl)piperidine,
1-(phenylmethoxycarbonyl)-4-hydroxy-4-tributylstannyl)piperidine,
1,2,3,6-tetrahydro-1-(1,1-dimethylethoxy-carbonyl)-4-tributylstannylpyridine,
1,2,3,6-tetrahydro-1-(phenylmethoxycarbonyl)-4-tributylstannylpyridine,
1-acetyl-2,6-dimethyl-4-hydroxy-4-tributylstannylpiperidine,
1-acetyl-2-methyl-4-hydroxy-4-tributylstannylpiperidine,
1,2,3,6-tetrahydro-1-acetyl-2,6-dimethyl-4-tributylstannylpyridine,
1,2,3,6-tetrahydro-1-acetyl-2-methyl-4-tributylstannylpyridine,
3-((1,1-dimethylethoxycarbonyl)amino)-1-tributylstannyl-1-cyclopentene,
3-(amino)-1-tributylstannyl-1-cyclopentene,
3-tributylstannyl-cyclopent-2-enone,
3-hydroxy-1-tributylstannyl-1-cyclopentene,
1-acetyl-4-hydroxy-4-(trimethylstannyl)piperidine,
1-(1,1-dimethylethoxycarbonyl)-4-hydroxy-4-(trimethylstannyl)piperidine,
1-(phenylmethoxycarbonyl)-4-hydroxy-4-trimethylstannyl)piperidine,
1,2,3,6-tetrahydro-1-(1,1-dimethylethoxycarbonyl)-4-trimethylstannylpyridine,
1,2,3,6-tetrahydro-1-(phenylmethoxycarbonyl)-4-trimethylstannylpyridine,
1-acetyl-2,6-dimethyl-4-hydroxy-4-trimethylstannylpiperidine,
1-acetyl-2-methyl-4-hydroxy-4-trimethylstannylpiperidine,
1,2,3,6-tetrahydro-1-acetyl-2,6-dimethyl-4-trimethylstannylpyridine,
1,2,3,6-tetrahydro-1-acetyl-2-methyl-4-trimethylstannylpyridine,
3-((1,1-dimethylethoxycarbonyl)amino)-1-trimethylstannyl-1-cyclopentene,
3-(amino)-1-trimethylstannyl-1-cyclopentene,
3-trimethylstannyl-cyclopent-2-enone,
3-hydroxy-1-trimethylstannyl-1-cyclopentene,
1-cyclopropyl-6,8-difluoro-1,4-dihydro-7-ol-4-oxo-3-quinolinecarboxylic acid,
1-ethyl-6,8-difluoro-1,4-dihydro-7-ol-4-oxo-3-quinolinecarboxylic acid,
3-ethyl-6-fluoro-1,4-dihydro-7-ol-4-oxo-3-quinolinecarboxylic acid,
1-(2,4-difluorophenyl)-6-fluoro-1,4-dihydro-7-ol-4-oxo-3-quinolinecarboxylic acid,
1-(2,4-difluorophenyl)-6,8-difluoro-1,4-dihydro-ol-4-oxo-3-quinolinecarboxylic acid,
1-cyclopropyl-6-fluoro-8-chloro-1,4-dihydro-7-ol-4-oxo-3-quinolinecarboxylic acid,
1-ethyl-6-fluoro-8-chloro-1,4-dihydro-7-ol-4-oxo-3-quinolinecarboxylic acid,
1-(2,4-difluorophenyl)-6-fluoro-8-chloro-1,4-dihydro-7-ol-4-oxo-3-quinolinecarboxylic acid,
1-cyclopropyl-5-amino-6,8-difluoro-1,4-dihydro-7-ol-4-oxo-3-quinolinecarboxylic acid,
9-fluoro-3-methyl-10-ol-7-oxo-2,3-dihydro-7H-pyrido[1,2,3-de][1,4]benzoxazine-6-carboxylic acid,
1cyclopropyl-7-trifluoromethylsulfonyloxy-6,8-difluoro-1,4-dihydro-4-oxo-3-quinolinecarboxylic acid ethyl ester,
1-cyclopropyl-7-trifluoromethylsulfonyloxy-6,8-difluoro-1,4-dihydro-4-oxo-3-quinolinecarboxylic acid methyl ester,
1-cyclopropyl-7-trifluoromethylsulfonyloxy-6-fluoro-1,4-dihydro-4-oxo-3-quinolinecarboxylic acid methyl ester,
1-ethyl-7-trifluoromethylsulfonyloxy-6,8-difluoro-1,4-dihydro-4-oxo-3-quinolinecarboxylic acid ethyl ester,
1-ethyl-7-trifluoromethylsulfonyloxy-6,8-difluoro-1,4-dihydro-4-oxo-3-quinolinecarboxylic acid methyl ester,
1-ethyl-7-trifluoromethylsulfonyloxy-6-fluoro-1,4-dihydro-4-oxo-3-quinolinecarboxylic acid ethyl ester, 1-ethyl-7-trifluoromethylsulfonyloxy-6-fluoro-1,4-dihydro-4-oxo-3-quinolinecarboxylic acid methyl ester,
1-(2,4-difluorophenyl)-7-trifluoromethyl-sulfonyloxy-6,8-difluoro-1,4-dihydro-4-oxo-3-quinolinecarboxylic acid ethyl ester,
1-(2,4-difluorophenyl)-7-trifluoromethylsulfonyloxy-6,8-difluoro-1,4-dihydro-4-oxo-3-quinolinecarboxylic acid methyl ester,
1-(2,4-difluorophenyl)-7-trifluoromethylsulfonyloxy-6-fluoro-1,4-dihydro-4-oxo-3-quinolinecarboxlic acid ethyl ester,
1-(2,4-difluorophenyl)-7-trifuoromethylsulfonyloxy-6-fluoro-1,4-dihydro-4-oxo-3-quinolinecarboxylic acid methyl ester,
9-fluoro-3-methyl-10-(trifluoromethylsulfonyl-oxy)-7-oxo-2,3-dihydro-7H-pyrido[1,2,3-de][1,4]benzoxazine-6-carboxylic acid ethyl ester, and
9-fluoro-3-methyl-10-(trifluoromethylsulfonyl-oxy)7oxy)-7-oxo-2,3-dihydro-7H-pyrido[1,2,3-de][1,4]benzoxazine-6-carboxylic acid methyl ester.

Most preferred intermediates in the above process include but are not limited to:
1-acetyl-4-hydroxy-4-(tributylstannyl)piperidine,
1,2,3,6-tetrahydro-1-acetyl-4-tributylstannylpyridine,
3-(phthalimido)-1-tributylstannyl-1-cyclopentene,
1,2,3,6-tetrahydro-1-acetyl-4-trimethylstannylpyridine,
3-(phthalimido)-1-trimethylstannyl-1-cyclopentene,
1-cyclopropyl-6-fluoro-1,4-dihydro-7-ol-4-oxo-3-quinolinecarboxylic acid, and
1-cyclopropyl-7-trifluoromethylsulfonyloxy6,86,8-difluoro-1,4-dihydro-4-oxo-3-quinolinecarboxylic acid ethyl ester.

Novel compounds prepared by the process described above are selected from the group consisting of:
1-cyclopropyl-6-fluoro-1,4-dihydro-4-oxo-7-1,2,3,6-tetrahydro-1-acetyl-4-pyridinyl)-3-quinolinecarboxylic acid methyl ester,
1-ethyl-6-fluoro-1,4-dihydro-4-oxo-7-(1,2,3,6-tetrahydro-4-pyridinyl)-3-quinolinecarboxylic acid,
1-ethyl-6-fluoro-1,4-dihydro-4-oxo-7-(1,2,3,6-tetrahydro-1-acetyl-4-pyridinyl)-3-quinolinecarboxylic acid ethyl ester,
1-ethyl-6-fluoro-1,4-dihydro-4-oxo-7-(1,2,3,6-tetrahydro-1-acetyl-4-pyridinyl)-3-quinolinecarboxylic acid methyl ester,
1-(2,4-difluorophenyl)-6-fluoro-1,4-dihydro-4-oxo-7-(1,2,3,6-tetrahydro-1-acetyl-4-pyridinyl)-3-quinolinecarboxylic acid methyl ester,
1-cyclopropyl-6-fluoro-1,4-dihydro-4-oxo-7-(1,2,3,6-tetrahydro-1-acetyl-4-pyridinyl)-1,8-naphthyridine-3-carboxylic acid methyl ester,
1-ethyl-6-fluoro-1,4-dihydro-4-oxo-7-(1,2,3,6-tetrahydro-4-pyridinyl)-1,8-naphthyridine-3-carboxylic acid,
1-ethyl-6-fluoro-1,4-dihydro-4-oxo-7-(1,2,3,6-tetrahydro-1-acetyl-4-pyridinyl)-1,8-naphthyridine-3-carboxylic acid ethyl ester,
1-ethyl-6-fluoro-1,4-dihydro-4-oxo-7-(1,2,3,6-tetrahydro-1-acetyl-4-pyridinyl)-1,8-naphthyridine-3-carboxylic acid methyl ester,
1-(2,4-difluorophenyl)-6-fluoro-1,4-dihydro-4-oxo-7-(1,2,3,6-tetrahydro-4-pyridinyl)-1,8-naphthyridine-3-carboxylic acid methyl ester,
9-fluoro-3-methyl-10-(1,2,3,6-tetrahydro-4-pyridinyl)-7-oxo-2,3-dihydro-7H-pyrido[1,2,3-de]-[1,4]benzoxazine-6-carboxylic acid,
9-fluoro-3-methyl-10-(1,2,3,6-tetrahydro-1-acetyl-4-pyridinyl)-7-oxo-2,3-dihydro-7H-pyrido[1,2,3-de][1,4]benzoxazine-6-carboxylic acid ethyl ester,
9-fluoro-3-methyl-10-(1,2,3,6-tetrahydro-1-acetyl-4-pyridinyl)-7-oxo-2,3-dihydro-7H-pyrido[1,2,3-de][1,4]benzoxazine-6-carboxylic acid methyl ester,
1-cyclopropyl-7-ethenyl-6,8-difluoro-1,4-dihydro-4-oxo-3-quinolinecarboxylic acid,
1-cyclopropyl-7-ethenyl-6,8-difluoro-1,4-dihydro-4-oxo-3-quinolinecarboxylic acid ethyl ester,
1-cyclopropyl-7-ethenyl-6,8-difluoro-1,4-dihydro-4-oxo-3-quinolinecarboxylic acid methyl ester,
1-ethyl-7-ethenyl-6,8-difluoro-1,4-dihydro-4-oxo-3-quinolinecarboxylic acid,
1-ethyl-7-ethenyl-6,8-difluoro-1,4-dihydro-4-oxo-3-quinolinecarboxylic acid ethyl ester,
1-ethyl-7-ethenyl-6,8-difluoro-1,4-dihydro-4-oxo-3-quinolinecarboxylic acid methyl ester,
1-(2,4-difluorophenyl)-7-ethenyl-6,8-difluoro1,4-dihydro-4-oxo-3-quinolinecarboxylic acid,
1-(2,4-difluorophenyl)-7-ethenyl-6,8-difluoro1,4-dihydro-4-oxo-3-quinolinecarboxylic acid ethyl ester,
1-(2,4-difluorophenyl)-7-ethenyl-6,8-difluoro1,4-dihydro-4-oxo-3-quinolinecarboxylic acid methyl ester,
1-cyclopropyl-7-ethenyl-6-fluoro-1,4-dihydro-4-oxo-3-quinolinecarboxylic acid methyl ester,
1-ethyl-7-ethenyl-6-fluoro-1,4-dihydro-4-oxo-3-quinolinecarboxylic acid,
1-ethyl-7-ethenyl-6-fluoro-1,4-dihydro-4-oxo-3-quinolinecarboxylic acid ethyl ester,
1-ethyl-7-ethenyl-6-fluoro-1,4-dihydro-4-oxo-3-quinolinecarboxylic acid methyl ester,
1-(2,4-difluorophenyl)-7-ethenyl-6-fluoro-1,4-dihydro-4-oxo-3-quinolinecarboxylic acid ethyl ester,
1-(2,4-difluorophenyl)-7-ethenyl-6-fluoro-1,4-dihydro-4-oxo-3-quinolinecarboxylic acid methyl ester,
1-cyclopropyl-7-ethenyl-6-fluoro-1,4-dihydro-4-oxo-1,8-naphthyridine-3-carboxylic acid methyl ester,
1-ethyl-7-ethenyl-6-fluoro-1,4-dihydro-4-oxo1,8-naphthyridine-3-carboxylic acid,
1-ethyl-7-ethenyl-6-fluoro-1,4-dihydro-4-oxo1,8-naphthyridine-3-carboxylic acid ethyl ester,
1-ethyl-7-ethenyl-6-fluoro-1,4-dihydro-4-oxo1,8-naphthyridine-3-carboxylic acid methyl ester,
1-(2,4-difluorophenyl)-7-ethenyl-6-fluoro-1,4-dihydro-4-oxo-1,8-naphthyridine-3-carboxylic acid ethyl ester,
1-(2,4-difluorophenyl)-7-ethenyl-6-fluoro-1,4-dihydro-4-oxo-1,8-naphthyridine-3-carboxylic acid methyl ester,
1-ethyl-6-fluoro-7-(3-amino-1-cyclopentenyl)-1,4-dihydro-4-oxo-3-quinolinecarboxylic acid,
1-ethyl-6-fluoro-7-((3-(1,1-dimethylethoxycarbonyl)amino)-1-cyclopentenyl)-1,4-dihydro-4-oxo-3-quinolinecarboxylic acid ethyl ester,
1-ethyl-6,8-difluoro-7-(3-amino-1-cyclopentenyl)-1,4-dihydro-4-oxo-3-quinolinecarboxylic acid,
1-ethyl-6,8-difluoro-7-((3-(1,1-dimethylethoxy)amino)-1-cyclopentenyl)-1,4-dihydro-4-oxo-3-quinolinecarboxylic acid ethyl ester, and
1-(2,4-difluorophenyl)-6,8-difluoro-7-((3-(1,1-dimethyl(ethoxylcarbonyl)-amino-1-cyclopentenyl)1,3-dihydro-4-oxo-3-quinolinecarboxylic acid ethyl ester.

Preferred compounds prepared by the above process are selected from the group consisting of:
1-(2,4-difluorophenyl)-6-fluoro-1,4-dihydro-4-oxo-7-(1,2,3,6-tetrahydro-4-pyridinyl)-3-quinolinecarboxylic acid,
1-(2,4-difluorophenyl)-6-fluoro-1,4-dihydro-4-oxo-7-(1,2,3,6-tetrahydro-1-acetyl-4-pyridinyl)-3quinolinecarboxylic acid ethyl ester, 1-(2,4-difluorophenyl)-6-fluoro-1,4-dihydro-4-oxo-7-(1,2,3,6-tetrahydro-4-pyridinyl)-1,8-naphthyridine-3-carboxylic acid, 1-(2,4-difluorophenyl)-6-fluoro-1,4-dihydro-4-oxo-7-(1,2,3,6-tetrahydro-1-acetyl-4-pyridinyl)-1,8-naphthyridine-3-carboxylic acid ethyl ester, 1-(2,4-difluorophenyl)-7-ethenyl-6-fluoro-1,4-dihydro-4-oxo-3-quinolinecarboxylic acid, 1-(2,4-difluorophenyl)-7-ethenyl-6-fluoro-1,4-dihydro-4-oxo-1,8-naphthyridine-3-carboxylic acid, 1-ethyl-6-fluoro-7-(3-amino-1-cyclopentenyl)-1,4-dihydro-4-oxo-1,8-naphthyridine-3-carboxylic acid, 1-ethyl-6-fluoro-7-((3-(1,1-dimethylethoxycarbonyl)amino)-1-carbonyl)amino)-1-cyclopentenyl)-1,4-dihydro-4-oxo1,8-naphthyridine-3-carboxylic -naphthyridine-3-carboxylic acid ethyl ester, 1-(2,4-difluorophenyl)-6-fluoro-7-(3-amino-1-cyclopentenyl)-1,4-dihydro-4-oxo-1,8-naphthyridine-3-carboxylic acid, 1-(2,4-difluorophenyl)-6-fluoro-7-((3-(1,1-dimethylethoxycarbonyl)amino)-1-cyclopentenyl)-1,4-dihydro-4-oxo-1,8-naphthyridine-3-carboxylic acid ethyl ester, 1-(2,4-difluorophenyl)-6-fluoro-7-(3-amino-1-cyclopentenyl)-1,4-dihydro-4-oxo-3-quinolinecarboxylic acid, 1-(2,4-difluorophenyl)-6-fluoro-7-((3-(1,1-dimethylethoxycarbonyl)amino)-1-cyclopentenyl)-1,4-dihydro-4-oxo-3-quinolinecarboxylic acid ethyl ester, 1-cyclopropyl-6,8-difluoro-7-(3-amino-1-cyclopentyl)-1,4-dihydro-4-oxo-3-quinolinecarboxylic acid, 1-cyclopropyl-6,8-difluoro-7-((3-(1,1-dimethyl- ethoxycarbonyl)amino)-1-cyclopentenyl)-1,4-dihydro-4-oxo-3-quinolinecarboxylic acid ethyl ester, and 1-(2,4-difluorophenyl)-6,8-difluoro-7-(3-amino-1-cyclopentenyl)-1,4-dihydro-4'-oxo-3-quinolinecarboxylic acid.

Most preferred compounds prepared by the above process are selected from the group consisting of:

1-cyclopropyl-6-fluoro-1,4-dihydro-4-oxo-7-(1,2,3,6-tetrahydro-4-pyridinyl)-3-quinolinecarboxylic acid, 1-cyclopropyl-6-fluoro-1,4-dihydro-4-oxo-7-(1,2,3,6-tetrahydro-1-acetyl-4-pyridinyl)-3-quinolineocarboxylic acid ethyl ester, 1-cyclopropyl-6-fluoro-1,4-dihydro-4-oxo-7-(1,2,3,6-tetrahydro-4-pyridinyl)-1,8-naphthyridine3-carboxylic acid, 1-cyclopropyl-6-fluoro-1,4-dihydro-4-oxo-7-(1,2,3,6-tetrahydro-1-acetyl-4-pyridinyl)-1,8-naphthyridine-3-carboxylic acid ethyl ester, 1-cyclopropyl-6-fluoro-1,4-dihydro-4-oxo-7-(1-(1-methoxy)ethenyl))-1,8-naphthyridine-3-carboxylic acid ethyl ester, 1-cyclopropyl-6,8-difluoro-1,4-dihydro-4-oxo-7(1-(1-methoxyethenyl))-3-quinolinecarboxylic acid ethyl ester, 1-cyclopropyl-6-fluoro-1,4-dihydro-4-oxo-7-(1-(1-methoxyethenyl))-3-quinolinecarboxylic acid ethyl ester, 1-cyclopropyl-7-ethenyl-6-fluoro-1,4-dihydro-4-oxo-3-quinolinecarboxylic acid, 1-cyclopropyl-7-ethenyl-6-fluoro-1,4-dihydro-4-oxo-3-quinolinecarboxylic acid ethyl ester, 1-cyclopropyl-7-ethenyl-6-fluoro-1,4-dihydro-4-oxo-1,8-naphthyridine-3-carboxylic acid, 1-cyclopropyl-7-ethenyl-6-fluoro-1,4-dihydro-4-oxo-1,8-naphthyridine-3-carboxylic acid ethyl ester, 1-cyclopropyl-6-fluoro-7-(3-amino-1-cyclopentenyl)-1,4-dihydro-4-oxo-1,8-naphthyridine-3-carboxylic acid, 1-cyclopropyl-6-fluoro-7-((3-(1,1-dimethylethoxycarbonyl)amino)-1-cyclopentenyl)-1,4-dihydro-4-oxo1,8-naphthyridine-3-carboxylic acid ethyl ester, 1-cyclopropyl-6-fluoro-7-(3-amino-1-cyclopentenyl)-1,4-dihydro-4-oxo-3-quinolinecarboxylic acid, and 1-cyclopropyl-6-fluoro-7-((3-(1,1-dimethylethoxycarbonyl)amino)-1-cyclopentenyl)-1,4-dihydro-4-oxo-3-quinolinecarboxylic acid ethyl ester.

The term lower alkyl means a straight or branched carbon chain of from one to four atoms unless otherwise specified. Representative of such groups are methyl, ethyl, propyl, isopropyl, t-butyl and the like.

The term cycloalkyl comprises those having from three to six carbon atoms such as cyclopropyl, cyclobutyl, cyclopentyl, and cyclohexyl.

The term alkenyl means a carbon chain of from two to ten atoms wherein a double bond is present, such as ethenyl or 1-propenyl.

The term alkynyl means an unsaturated aliphatic radical of from two to ten carbon atoms containing a triple bond.

The term aryl means an aromatic six-membered ring containing carbon or nitrogen and may be substituted with carbon radicals and heteroatoms.

The term halogen is intended to include fluorine, chlorine, bromine, and iodine unless otherwise specified.

Certain compounds of the invention may exist in optically active forms. The pure D isomer, pure L isomer, as well as mixtures thereof, including the racemic mixtures, are contemplated by the invention. Additional asymmetric carbon atoms may be present in a substituent group such as a tetrasubstituted carbon. All such isomers, and diastereomers as well as mixtures thereof, are contemplated by the invention.

The compounds of the invention display antibacterial activity when tested by the microdilution method as described in Heifetz, et al, *Antimicr. Agents and Chemoth.*, 6, 124 (1974), which is incorporated herein by reference.

By use of this method, the following minimum inhibitory concentration values (MICs in μg/ml) were obtained for representative compounds of the invention.

| In Vitro Antibacterial Activity Minimal Inhibitory Concentration MIC (μg/ml) | | |
|---|---|---|
| Organism | Compound 10 | Compound 5 |
| E. cloacae | 12.5 | 0.1 |
| E. coli | 12.5 | 0.2 |
| K. pneumoniae | 25 | 0.4 |
| P. rettgeri | >25 | 0.4 |
| P. aeruginosa | >25 | 1.6 |
| S. aureus | 6.3 | ≦0.025 |
| S. aureus | 6.3 | ≦0.025 |
| S. faecalis | 25 | 0.2 |
| S. pneumoniae | 12.5 | 0.8 |
| S. pyogenes | 12.5 | 0.8 |
| E. coli | 12.5 | 0.1 |

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like.

Examples of suitable amines are N,N'-dibenzylethylenediamine, chloroprocaine, choline, diethanolamine, ethylenediamine, N-methylglucamine, procaine, triethylamine, and the like.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, lactic, succinic, ascorbic, maleic, methanesulfonic, all amino acids such as glycine, alanine, phenylalanine and the like. The salts are prepared by contacting the free base form with a sufficient amount of the desired acid to produce either a mono or di salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where $R_2$ is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

The compounds of the invention can be prepared and administered in a wide variety of oral and parenteral dosage forms. It will be obvious to those skilled in the art that the following dosage forms may comprise as the active component, either a compound of formula I or a corresponding pharmaceutically acceptable salt of a compound of formula I.

For preparing pharmaceutical compositions from the compounds described by this invention, inert, pharmaceutically acceptable carriers can be either solid or liquid. Solid form preparation include powders, tablets, dispersible granules, capsules, cachets, and suppositories. A solid carrier can be one or more substances which may also act as diluents, flavoring agents, solubilizers, lubricants, suspending agents, binders, or tablets disintegrating agents; it can also be an encapsulating material. In powders, the carrier is a finely divided solid which is in admixture with the finely divided active compound. The table the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the packaging containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

SCHEME I
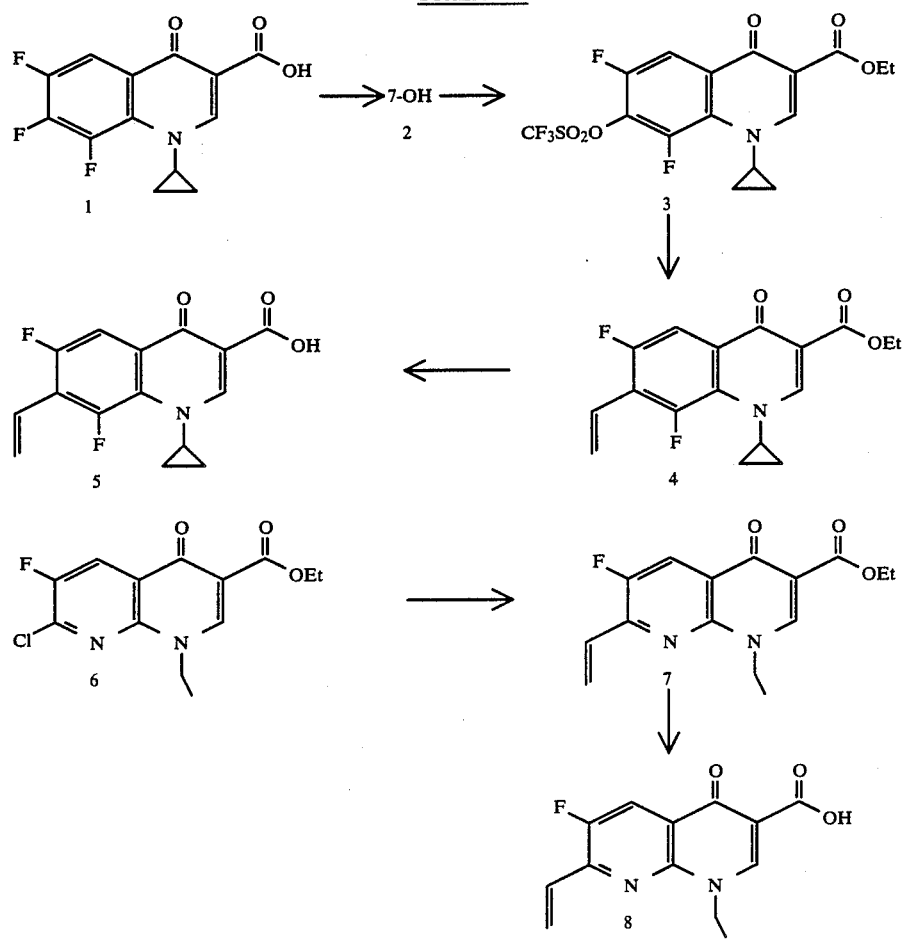
SCHEME II
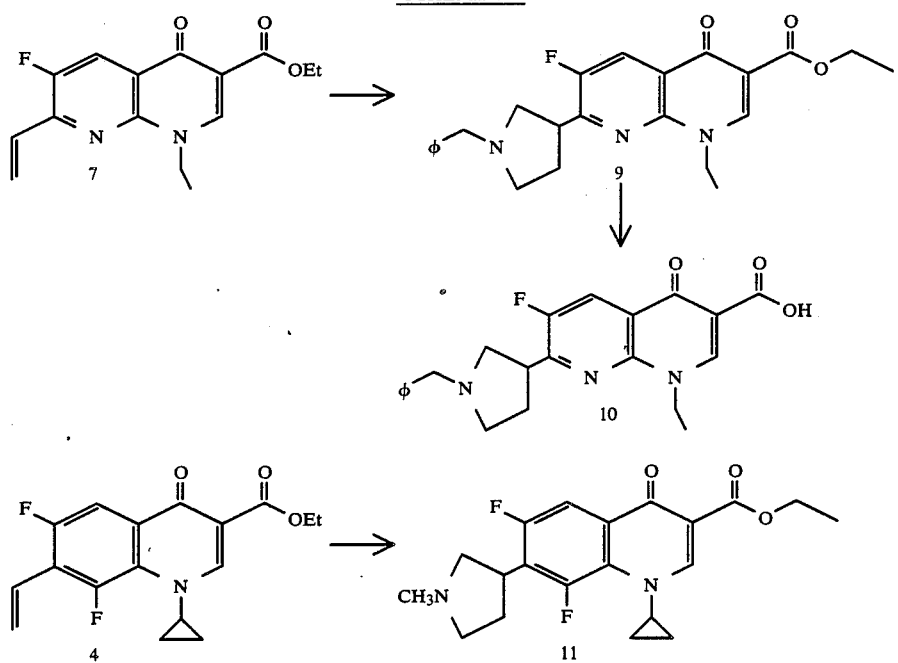

SCHEME III
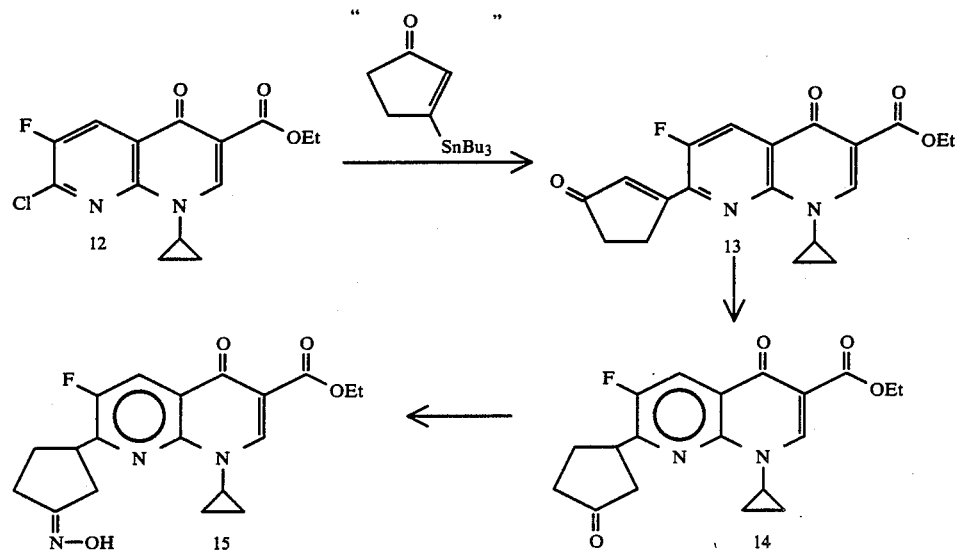
SCHEME IV
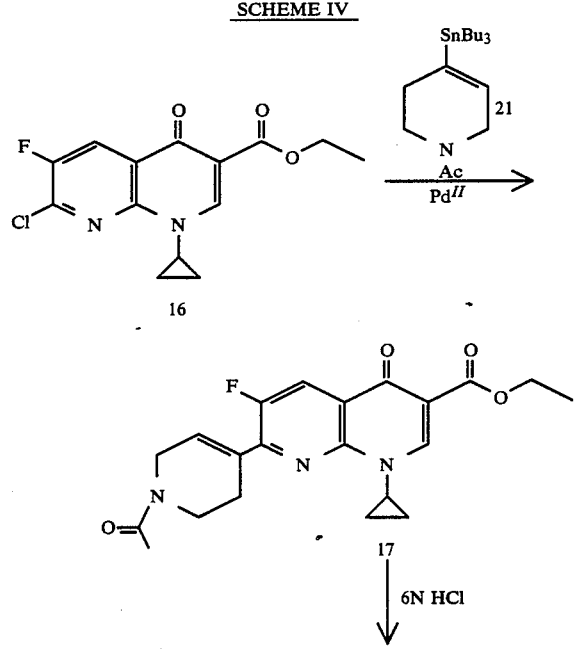
-continued-
SCHEME IV
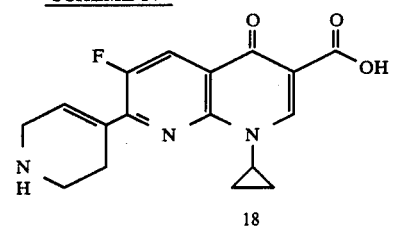
SCHEME V
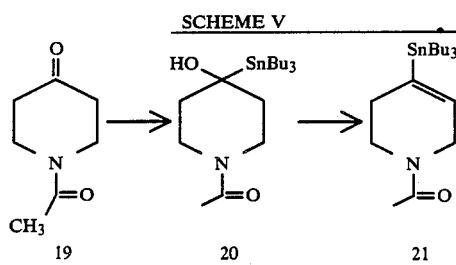
SCHEME VI
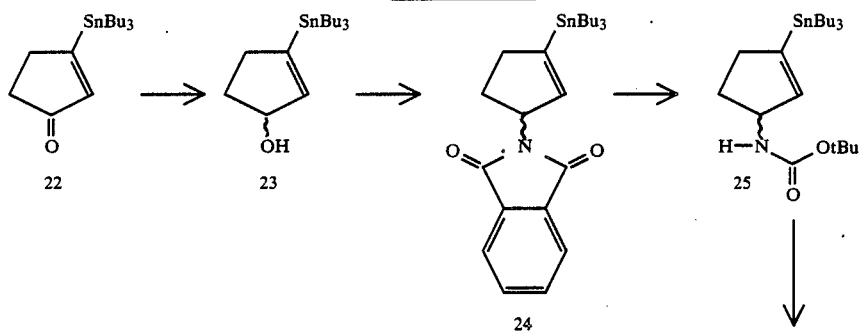

SCHEME VI

-continued

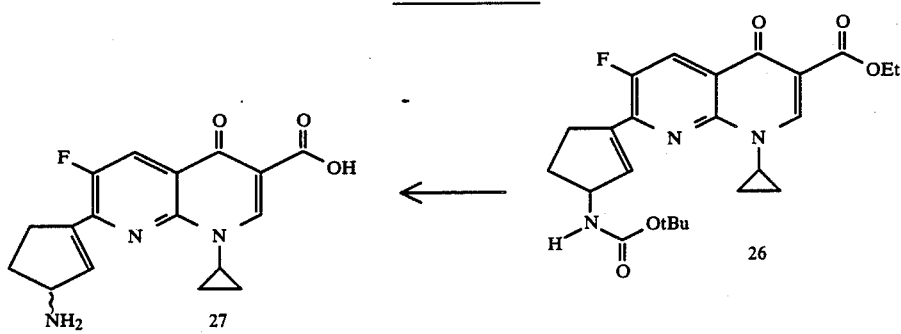

The following nonlimiting examples illustrate the processes of the present invention.

EXAMPLE 1

1-Cyclopropyl-6,8-difluoro-1,4-dihydro-7-ol-4-oxo-3-quinoline carboxylic acid (2)

Into a properly equipped flask was placed 50 g of 1-cyclopropyl-6,7,8-trifluoro-1,4-dihydro-4-oxo-quinolinecarboxylic acid (1), 1000 ml 1N NaOH, and 200 ml THF. The solution was heated to reflux overnight. After 24 hours the yellow solution was allowed to cool to room temperature and was filtered to remove any solids. HCl was added (6N at first and then 1N) until pH 4–5 was reached, and the solid which came out was collected by filtration and washed with water at pH 4. The solid was dried to give 49.3 g of a yellow solid 99.6%.

IR (KBR)-1711, 1619, 1470, 1325, 1034, 809, 670 cm$^{-1}$

NMR (DMSO)-ppm 14.85 (s broad, 1H); 12.3–11.8 (s very broad, 1H); 8.66 (s, 1H); 7.85 (dd, 2H J=10.5 Hz, 2.0 Hz); 4.13 (m, 1H); 1.20 (m, 4H). MS-M+ =281.1, M —CO$_2$=237.1.

1-Cyclopropyl-6-fluoro-1,4-dihydro-7-ol-4-oxo-3-quinolinecarboxylic acid

This compound was prepared by the method in Example 1.

Anal. for $C_{13}H_{10}FNO_4 \cdot 0.44H_2O$: Calcd: C 56.23; H 4.21; N 5.04. Found: C 56.21; H 3.61; N 5.02.

EXAMPLE 2

1-Cyclopropyl-7-trifluoromethylsulfonyloxy-6,8-difluoro-1,4-dihydro-4-oxo-3-quinolinecarboxylic acid ethyl ester (3)

Into a properly equipped flask was placed 4.0 g (14.22 mmoles) of Compound 2 along with 50 ml of dry pyridine. Under a flow of nitrogen, 12.04 g (42.66 mmoles) of trifluoromethanesulfonic anhydride was added via syringe while stirring in an ice bath. The solution was then allowed to warm to room temperature and became dark brown and homogeneous. The reaction was monitored using TLC by quenching aliquots in EtOH. After 5.5 hours, the reaction was quenched with 22 ml EtOH (375 mmoles) and allowed to stir at room temperature for 20 minutes, until TLC showed reaction was complete. The reaction was poured into water and the precipitate collected and washed with water. After drying, 3.9 g (62%) of Compound 3 was obtained.

IR (Kbr)-3600–3200, 1733, 1621, 1482, 1244, 1138, 804, 645 cm$^{-1}$. NHR (CDCl$_3$)-ppm 8.56 (s, 1H); 8.12 (dd, 1H, J=7.0 Hz, 2.0 Hz); 4.33 (q, 2H, J=7.1 Hz); 3.84 (m, 1H); 1.34 (t, 3H, J=7.1 Hz); 1.25 (m, 2H); 1.11 (m, 2H). MS-M+=440.9.

1-Cyclopropyl-7-trifluoromethylsulfonyl-6-fluoro-1,4-dihydro-4-oxo-3-quinolinecarboxylic acid ethyl ester This compound was prepared by the method in Example 2.

Anal. for $C_{16}H_{13}F_4NO_6S$: Calcd: C 45.41; H 3.10; N 3.31. Found: C 45.63; H 3.04; N 3.21.

EXAMPLE 3

1-Cyclopropyl-7-ethenyl-6,8-difluoro-1,4-dihydro-4-oxo-3-quinolinecarboxylic acid ethyl ester (4)

Into a properly equipped flask was added 2.0 g (4.52 mmoles) Compound 3 and 24 ml dry THF. While flushing with nitrogen, 1.36 ml (4.68 mmoles) of vinyltributyltin was added along with 0.58 g (13.56 mmoles) LiCl and, 0.070 g (0.10 mmoles) Pd(PPh$_3$)$_2$Cl$_2$. A couple crystals of 2,6-di-tert-butyl4-methyl phenol was also added just before heating. The reaction was heated to 60°–65° C. for 21 hours after which it turned black and a black precipitate was present. The reaction was cooled to room temperature and 1 ml of pyridine and 2 ml of pyridinium fluoride were added and the reaction allowed to stir overnight. THF was added and the reaction filtered through a celite pad and poured into water. The precipitate formed was collected to give 2.0 g of crude product which was taken up in CH$_2$Cl$_2$ and run through a short silica gel column eluting with dichloromethane to start and slowly increasing polarity to 1% methanol in dichloromethane. The fractions containing product were evaporated in vacuo to give 1.07 g of (4), 74% yield.

IR (Kbr)-3600–3200, 1728, 1698, 1641, 1421, 1251, 1191, 802 cm$^{-1}$. NMR (CDCl$_3$)-ppm 8.60 (s, 1H); 7.97 (dd, 1H, J=10.8 Hz, 1.8 Hz); 6.82 (dd, 1H, J=18.0 Hz, 12.0 Hz); 6.21 (d, 1H, J=18.0 Hz); 5.79 (d, 1H, J=12.0 Hz); 4.39 (q, 2H, J=7.0 Hz); 3.92 (m, 1H); 1.40 (t, 3H, J=7.0 Hz); 1.3–1.1 (m, 4H). MS-M+=319.1.

Anal. for $C_{17}H_{16}F_2NO_3 \cdot 0.3H_2O$: Calcd: C 62.87; H 4.84; N 4.31; F 11.70. Found: C 62.91; H 5.04; N 3.92; F 11.49.

1-Cyclopropyl-7-ethenyl-6-fluoro-1,4-dihydro-4-oxo-3-quinolinecarboxylic acid ethyl ester This compound was prepared by the method in Example 3.

Anal. for $C_{17}H_{16}FNO_3 \cdot 0.55CH_3OH$: Calcd: C66.09; H 5.10; N 4.39. Found: C 66.09; H 5.10; N 4.39.

1-Cyclopropyl-7-(1-(1-methoxyethenyl))-6,8-difluoro-1,4-dihydro-4-oxo-3-quinolinecarboxylic acid ethyl ester This compound was prepared by the method in Example 3 using (1-methoxyethenyl)tributylstannane.

NMR (CDCl$_3$) ppm - 8.60 (s, 1H), 8.00 (dd, J=9Hz, J=2Hz, 1H), 4.69 (d, J=3Hz, 1H), 4.44 (d, J=3Hz, 1H), 4.39 (q, J=7Hz, 2H), 3.82–3.97 (m, 1H), 3.77 (s, 3H), 1.41 (t, J=7 Hz, 3H), 1.06–1.34 (m, 4H).

MS - M$^+$ = 349, 277 (base).

IR 1731, 1696, 1622, 1551, 1482, 1325, 1242, 803.

1-Cyclopropyl-7-(1-(1-methoxyethenyl))-6-fluoro-1,4-dihydro-4-oxo-1,8-naphthyridine-3-carboxylic acid ethyl ester This compound was prepared by the method in Example 3 using (1-methoxyethenyl)tributylstannane.

Anal. for C$_{17}$H$_{17}$FN$_2$O$_4$: Calcd: C 61.44; H 5.16; N 8.43; F 5.72. Found: C 61.67; H 5.15; N 8.37; F 6.13.

Melting Point 151°–152.5° C.

EXAMPLE 4

1-Cyclopropyl-7-ethenyl-6,8-difluoro-1,4-dihydro-4-oxo-3-quinolinecarboxylic acid.(5)

Into a properly equipped flask was placed 0.30 g (0.939 mmoles) of Compound 4 along with 10 ml THF, 10 ml EtOH, 5 ml water, and 5 ml 1N NaOH. The mixture was refluxed for three hours after which TLC showed no starting material remained. The reaction was cooled and any residual solids removed by filtration. The filtrate was acidified to pH 4 where a solid precipitated. The yellow solid was filtered and dried to yield 0.19 g 70%.

IR (KBr)-3056, 2800-2600, 1625, 1501, 1472, 1114, 957, 810 cm$^{-1}$. NMR (DMSO)-ppm 14.47 (s, 1H); 8.75 (s, 1H); 7.91 (dd, 1H, J=10.5 Hz, 1.8 Hz); 6.89 (dd, 1H, J=18.0 Hz, 12.0 Hz); 6.20 (d, 1H, J=18.0 Hz); 5.95 (d, 1H, J=12.0 Hz); 4.18 (m, 1H); 1.23 (m, 4H).

MS-M$^+$=291.0.

Anal. for C$_{15}$H$_{11}$F$_2$NO$_3$: Calcd: C 61.86; H 3.81; N 4.81. Found: C 61.83; H 3.76; N 4.69.

1-Ethyl-7-ethenyl-6-fluoro-1,4-dihydro-4-oxo-1,8-naphthyridine-3-carboxylic acid (8)

This compound was prepared by the method in Example 4.

EXAMPLE 5

1-Ethyl-7-ethenyl-6-fluoro-1,4-dihydro-4-oxo-1,8-naphthyridine-3-carboxylic acid ethyl ester(7)

Into a properly equipped flask was placed 0.80 g (2.7 mmoles) Compound 6 along with 20 ml dry dioxane. While flushing with nitrogen 0.88 ml (2.8 mmoles) of vinyltributyltin was added along with 0.04 g (0.06 mmoles) PD(PPh$_3$)$_2$Cl$_2$. One or two crystals of 2,6-di-tert-butyl-4-methyl phenol was added just before heating. The reaction was heated to 90°–95° C. for 6 hours and then cooled to room temperature and 1 ml pyridine and 2 ml pyridinium fluoride added and the reaction stirred at room temperature overnight. The next day THF was added and the reaction filtered through a celite pad into water where a precipitate formed and was collected to give 0.1 g of solid.

IR (Kbr)-3600–3200, 2980, 1689, 1610, 1430, 1390, 1224, 1097, 807 cm$^{-1}$. NMR (CDCl$_3$)-ppm 8.66 (s, 1H); 8.40 (d, 1H, J=9.5 Hz); 7.14 (dd, 1H, J=17.3 Hz, 6.63 (d, 1H, J=17.3 Hz); 5.81 (d, 1H, J=10.9 Hz); 4.51 (q, 2H, J=7.2 Hz); 4.42 (q, 2H, J=7.1 Hz); 7.1 Hz); 1.54 (t, 3H, J=7.1 Hz); 1.42 (t, 3H, J=7.2 Hz). MS-M$^+$=290, 245, 218 (base).

Anal. for C$_{15}$H$_{15}$FN$_2$O$_3$: Calcd: C 62.06; H 5.21; N 9.65; F 6.54. Found: C 61.82; H 5.22; N 9.48; F 6.97.

1-Cyclopropyl-7-ethenyl-6-fluoro-1,4-dihydro-4-oxo1,8-naphthyridine-3-carboxylic acid ethyl ester The compound was prepared by the method in Example 5, mp 168.5° C. dec.

NMR (CDCl$_3$)-ppm 1.02–1.17 (m,2H), 1.23–1.57 (m,5H), 1.62–1.82 (m, $_1$h), 4.44 (d, 2H, J=7.1), 5.81 (dd, 1H, J=10, 1.8), 6.70 (dd, 1H, J=17, 1.8), 7.15 (dd, 1H, J=17, 10), 8.37 (d, 1H, J=9.4) 8.70 (S, 1H).

MS-M$^+$=302 230 (base).

EXAMPLE 6

1-Ethyl-6-fluoro-1,4-dihydro-4-oxo-7-[phenylmethyl-3pyrroliinyl]-1,8-naphthyridine-3-carboxylic acid ethyl ester (9)

1-Ethyl-7-ethenyl-6-fluoro-1,4-dihydro-4-oxo-1,8-naphthyridine-3-carboxylic acid ethyl ester (7) (0.45 g, 0.0015 mol), n-benzylglycine (0.65 g, 0.0039 mol), and paraformaldehyde (0.22 g, 0.0078 mol) were suspended in toluene (20 ml). The suspension was heated at reflux for 90 minutes with a Dean-Stark trap to remove the water formed. The reaction was cooled and evaporated and the residue purified by preparative TLC on silica gel eluted with 5% absolute ethanol in methylene chloride. The product band was scrapped from the plate and the product extracted with ethanol/methylene chloride. The solvents were evaporated to give 0.4 g of the title compound (9) as a yellow oil.

Ms-M$^+$=423, 332 (M$^+$-C$_7$H$_7$), 91 (base).

NMR (CDCl$_3$) 1.25–1.40 (m, 6H), 2.1–3.0 (m, 7H), 3.65(AB quart., 2H), 4.24 (q, 2H), 4.48 (q, 2H), 7.20–7.34 (m, 5H), 8.20 (d, 1H), 8.87 (s, 1H). IR (cm$^{-1}$, LF) 1732, 1695, 1643, 1619, 1420, 1222, 810, 701.

EXAMPLE 7

1-Ethyl-6-fluoro-1,4-dihydro-4-oxo-7-1-(phenylmethyl)-3-pyrrolidinyl]-1,8-naphthyridine-3-carboxylic acid (10)

Compound g (0.4 g, 0.001 mol) was dissolved in ethanol (5 ml) and 1N NaOH solution (2.0 ml, 0.002 mol) was added. The resulting solution was stirred for 90 minutes. The reaction was quenched by the addition of 1N HCl solution (2 ml) and evaporated to an oil. This oil was partitioned between methylene chloride and saturated NaCl solution. The NaCl layer was further extracted with methylene chloride. The combined organic layers were dried (MgSO$_4$), filtered, and evaporated to give an orange solid. This solid was dissolved in hot tetrahydrofuran and precipitated from solution by addition of ethyl ether. The collected solid was dissolved in methylene chloride and reprecipitated by addition of ethyl ether to give the title compound as a yellow solid (0.1 g).

MS-M$^+$=395, 351 (M$^+$-CO$_2$), 304 (M$^+$-C$_7$H$_7$), 260, 147, 91 (C$_7$H$_7$, base).

EXAMPLE 8

1-Cyclopropyl-6,8-difluoro-1,4-dihydro-7-(1-methyl-3-pyrroliidinyl)-4-oxo-1-cyclopropyl-3-quinolinecarboxylic acid ethyl ester (11)

1-Cyclopropyl-6,8-difluoro-1,4-dihydro-7-ethenyl-4-oxo-3-quinolonecarboxylic acid ethyl ester (4) (0.50 g, 0.0014 mol), sarcosine (1.14 g, 0.0124 mol), and paraformaldehyde (0.39 g, 0.0124 mol) were suspended in toluene and the suspension refluxed for 90 minutes with a Dean-Stark trap to collect the water formed. An additional 1.14 g of sarcosine and 0.39 g of paraformaldehyde were added and the reflux continued for 90 minutes. The reaction was cooled and the toluene solution was decanted from the brown solids.

Evaporation of the toluene gave a yellow solid. This solid was purified by chromatography on silica gel using methylene chloride as eluent to give the title compound (11) as a yellow solid (0.08 g).

MS-M+=376, 57 ($C_3H_7N$, base).

NMR ($CDCl_3$) 1.10-1.31 (m, 4H), 1.40 (t, 3H), 2.10-2.25 (m, 1H), 2.35-3.30 (M, 7H), 4.38 (q, 2H), 7.96 (dd, 1H), 8.60 (s, 1H).

EXAMPLE 9

1-Cyclopropyl-6-fluoro-1,4-dihydro-4-oxo-7-[1-methyl-3-pyrrolidinyl-1,8-naphthyridine-3-carboxylic acid

In a manner analogous to that employed to prepare Compound 9 (Examples 6 and 7), Compound 8 (0.4 g) was reacted with sarosine (0.35 g) and paraformaldehyde (0.12 g) to give the cycloaddition compound in 85% yield after this was purified by flash chromatography. This intermediate product was hydrolyzed with NaOH in ethanol, then acidified to pH 7 and evaporated to a gum. The gum was dissolved in 1N NaOH (3 ml) and diluted with 5 ml of $H_2O$. This solution after acidification to pH 7 was extracted with $CH_2Cl_2$ (10×50 ml). The combined $CH_2Cl_2$, dried over $MgSO_4$, filtered, and evaporated to give a pale yellow solid. This solid was dissolved in ethanol and evaporated to give 0.2 g of the title compound, mp 155°-160° C. dec.

Anal. for $C_{17}H_{18}FN_3O_3 \cdot 0.45\ H_2O$: Calcd: C 60.15, H 5.61, N 12.38 Found: C 60.06, H 5.41, N 12.39.

EXAMPLE 10

1-Cyclopropyl-6-fluoro-1,4-dihydro-4-oxo-7-(3-oxocyclopentyl)-1,8-naphthyridine-3-carboxylic acid ethyl ester (13)

Into a properly equipped flask was added 2.49 g (8.02 mmoles) of Compound 12 along with 50 ml dry THF. While flushing with nitrogen 3.08 g (8.30 mmoles) of 3-tributylstannyl cyclopentenone was added in 10 ml THF along with 0.12 g (0.17 mmoles) $Pd(PPh_3)_2Cl_2$. A couple crystals of 2,6-di-tert-butyl-4-methyl phenol was added just before heating. The reaction was heated to 60°-65° C. for 28 hours and then cooled to room temperature and 4 ml pyridine and 8 ml pyridinium fluoride solution were added and the reaction stirred for 14 hours. Ethyl ether was added and the reaction filtered and washed with THF. This greenish yellow solid was dried to give pure product 2.14 g, Compound 13 (75% yield).

IR (KBr) - 3600-3300 weak, 1712, 1611, 1426, 1242, 810 $cm^{-1}$. NMR ($CDCl_3$) - ppm 8.75 (s, 1H); 8.49 (d, 1H J=10.3 Hz); 7.12 (m, 1H); 4.42 (q, 2H J=7.1 Hz); 3.7 (m, 1H); 3.31 (m, 2H); 2.62 (m, 2H); 1.42 (t, 3H J=7.1 Hz); 1.34 (m, 2H); 1.10 (m, 2H). MS - M+=356.

Anal. for $C_{19}H_{17}FN_2O_4$: Calcd: C 64.04, H 4.81, N 7.86. Found: C 63.97, H 5.15, N 7.42.

EXAMPLE 11

1-Cyclopropyl-6-fluoro-1,4-dihydro-4-oxo-7-(3-oxo1-cyclopentan-1-yl)-1,8-naphthyridine-3-carboxylic acid ethyl ester (14)

Into a properly equipped flask was added 0.50 g (1.4 mmoles) Compound 13 along with 200 mg $(PP_3)_3RhCl$ and 75 ml THF. A 51 psi initial hydrogen pressure was used and a pressure drop of 5.4 psi indicated that the reaction was complete in less than two hours. The resultant brown solution was chromatographed on a small silica gel column to remove catalyst and 0.28 g (57%) was obtained of Compound 14.

NMR ($CDCl_3$) - ppm 8.7 (s, 1H); 8.4 (d, 1H); 4.4 (q, 2H); 4.1 (m, 1H); 3.6 (m, 1H); 2.9-2.2 (m, 6H); 1.4 (t, 3H); 1.3 (m, 2H); 1.0 (m, 2H).

EXAMPLE 12

7-(3-Oximinocyclopentyl)-1-cyclopropyl-6-fluoro-1,4-dihydro-4-oxo-1,8-naphthyridine-3-carboxylic acid ethyl ester (15)

Into a properly equipped flask was placed Compound 14 along with hydroxylamine hydrochloride (0.23 g, 3.3 mmol), sodium carbonate (0.37 g, 3.6 mmol), water, and ethanol. The reaction mix was stirred for 48 hours and the product 15 isolated by chromatography on a silica gel column.

NMR ($CDCl_3$) - ppm 8.7 (s, 1H), 8.4 (d, 1H), 4.3 (q, 2H), 3.8 (m, 1H), 3.6 (m, 1H), 3.0-2.5 (m, 4H), 2.35-2.2 (m, 1H), 2.15-1.95 (m, 1H), 1.3 (t, 3H), 1.2 (m, 2H), 7.0 (m, 2H).

EXAMPLE 13

1-Cyclopropyl-6-fluoro-1,4-dihydro-4-oxo-7-(1,2,3,6-tetrahydro-1-acetyl-4-piperidinyl)-1,8-naphthyridine-3-carboxylic acid ethyl ester (17)

Chloronaphthyridine 16 (8.00 g, 25.7 mmol), and tributylvinylstannane 21 (12.0 g, 28.9 mmol) were dissolved in THF (130 ml) then flushed with nitrogen. Bis(triphenylphosphine)palladium dichloride (0.36 g, 0.5 mmol) and 2,6-di-t-butyl-4-methylphenol (~10 mg) were added to the reaction mixture. This orange solution was refluxed for 36 hours, then cooled and stirred at room temperature for 48 hours. The reaction mixture was evaporated and the residue was purified by chromatography on silica gel with methylene chloride/methanol. The product fractions were recrystallized from THF to give 1.69 g of the title compound.

MS-M+=399, 356, 327, 82, 43 (base). NMR ($CDCl_3$)-ppm 8.69 (s, 1H), 8.65 (dd, 1H, J=1, 15.5 Hz), 2.02-6.92 (m, 1H), 4.43-4.26 (m, H), 3.72 (apparent t, 1H), 3.67-3.61 (apparent t+m, 2H), 2.37-2.84 (m, 1H), 2.18 (m, 3H), 1.41 (5, 7 Hz), 1.37-1.03 (m, 4H).

EXAMPLE 14

1-Cyclopropyl-6-fluoro-1,4-dihydro-4-oxo-7-(1,2,3,6-tetrahydro-4-pyridinyl)-1,8-naphthyridine-3-carboxylic acid (18)

The N-acetyl compound 17 (0.80 g) was dissolved in 6N HCl (30 ml) and heated to ~90° C. for 3 hours, then cooled and evaporated to a yellow solid. This solid was resuspended in water (30 ml) and 6N HCl (20 ml)

added. The thick slurry formed was collected by filtration and dried to give a pale yellow solid. The yield was 0.48 g of the title compound, 18.

NMR (DMSO) - ppm 9.4 (br s, 2H), 8.86 (s, 1H), 8.53 (d, 1H), 7.05 (br s, 1H), 3.9 (br s, 1H), 3.8 (m, 1H), 3.6-3.2 (m, H$_2$O +2H), 2.9 (m, 2H), 1.3-1.1 (m, 4H).

MS-M+=329 (base), 285, 270.

Anal. for C$_{17}$H$_{16}$FN$_3$O$_3$.HCl.1.25 H$_2$O: Calcd: C 52.58; H 5.06; N 10.82; Cl 9.13, H$_2$O 5.80. Found: C 52.57, H 4.86, N 10.76, Cl 9.40, H$_2$O 5.26.

EXAMPLE 15

1-Acetyl-4-hydroxy-4-(tributylstannyl)piperidine (20)

Di-isopropyl amine (11.9 ml, 85 mmol) was dissolved in THF (200 ml) and cooled to 0° C. and n-butyllithium (2M, 42 ml, 85 mmol) was added over one minute. This solution was stirred at 0° C. for 15 minutes and tributyltin hydride (22.8 ml, 85 mmol) was added over one minute to give a yellow solution. After 45 minutes at 0° C. the solution was cooled to −70° C. and 1-acetyl-4-piperidone (10.2 g, 71 mmol) in THF (60 ml) was added to the solution dropwise. Upon completion of this addition, the reaction mixture had become difficult to stir and an additional 100 ml of THF was added, and stirring continued at −70° for 2.5 hours. At −70° C. the reaction was quenched by addition of sodium dihydrogen phosphate buffer, pH 6.5. The reaction was allowed to warm to 0° C. This slurry was diluted with diethylether (600 ml) and water. The organic layer was separated, washed with NaCl solution, dried over MgSO$_4$, and evaporated to give the crude product. This was purified by flash column chromatography on silica gel using methylene chloride and 9/1 methylene chloride-ethanol. Evaporation of the appropriate fractions gave 16.4 g of the title compound, 20, which was used without further characterization.

NMR (CDCl$_3$) - ppm 4.0-3.1 (m, 4H), 3.0-2.7 (m, 1H), 2.1 (s, 3H), 2.0-0.8 (m, 31H).

EXAMPLE 16

1,2,3,6-Tetrahydro-1-acetyl-4-tributylstannyl-pyridine (21)

1-Acetyl-4-hydroxy-4-tributylstannyl-piperidine, 20 (16.4 g, 38 mmol) and triethylamine (15.0 ml, 108 mmol) were dissolved in methylene chloride (250 ml) and the solution cooled to 0° C. Methanesulfonylchloride (6.0 ml, 50 mmol) in methylene chloride (50 ml) was added dropwise to the cooled solution and the mixture was allowed to warm to room temperature and stir for 60 hours. The reaction solution was washed with NaCl solution, dried (MgSO$_4$), filtered, and evaporated to give a red oil which was purified by flash column chromatography on silica gel, eluting with 3% ethanol in CH$_2$Cl$_2$. After combining the appropriate fractions and evaporating the solvent, the title compound, 21, was obtained (7.5 g).

NMR (CDCl$_3$) - ppm 5.78-5.71 (m, 1H), 4.07 (m, 1H), 3.95 (m, 1H), 3.63 (m, 1H), 3.48 (m, 1H), 2.35-2.28 (br m, 1H), 2.10 and 2.08 (s, 3H), 1.51-1.42 (m, 6H), 1 37-1.26 (m, 6H), 0.89-0.82 (m, 15H).

MS-M+=414, 358 (base), 302, 246, 177, 124, 82.

EXAMPLE 17

3-Tributylstannyl-cyclopent-2-enone (22)

3-Ethoxy-cyclopent-2-enone (1.0 g, 7.9 mmol) was dissolved in THF (2 ml) and was placed in an addition funnel atop a flask equipped with stirring and a cooling bath. The flask was charged with THF (10 ml) and diisopropylamine (0.88 g, 8.7 mmol) and cooled to 0° C. To the solution was added n-butyllithium (1.9M, 4.6 ml) and the resulting solution stirred for five minutes. While still at 0° C., tributyltinhydride (2.35 ml, 8.7 mmol) was added to give a yellow solution, then after 15 minutes at 0° C., the solution was cooled to −70° C. At −70° C. the 3-ethoxy-cyclopent-2-enone was added dropwise, and after addition was complete, the reaction was stirred at −20° for one hour. The cooling bath was removed and the reaction quenched with NH$_4$Cl solution and diluted with ether. The organic layer was separated, dried (MgSO$_4$), filtered, and evaporated to give an oil. Chromatography on silica gel with CH$_2$Cl$_2$ gave the title compound (1.8 g).

NMR (CDCl$_3$) δ 6.4 (m, 1H), 2.8 (m, 2H), 2.3 (m, 2H), 1.5-0.7 (m, 39H).

EXAMPLE 18

3-Tri-n-butylstannyl-2-cyclopentenol (23)

A solution of cyclopentenone (27) (6.7 g, 18.0 mmol) in anhydrous ether (25 ml) was added dropwise to a stirred suspension of lithium aluminum hydride (0.38 g, 10.0 mmol) in dry ether (75 ml) at −30° C. The suspension was stirred between −30° C. and 0° C. for 2 hours, and then quenched by slow addition of a 1:1 mixture of saturated aqueous ammonium sulfate and water (20 ml). The resulting precipitate was filtered, washed with ethyl acetate (2×10 ml), and the combined filtrate and washings were dried over anhydrous magnesium sulfate. Filtration and evaporation of the solvent provided the title compound as a colorless liquid (6.20 g, 92%).

IR (liquid film) - 670, 1046, 1377, 3300-3550 cm$^{-1}$. $^1$H-NMR (CDCl$_3$) 0.75-1.08 (m, 15H), 1.13-1.39 m, 6H), 1.42-1.71 (m, 7H), 2.13-2.22 (m, 1H), 2.23-2.35 (m, 1H), 2.36-2.69 (m, 1H), 4.84-4.90 (m, 1H), 5.96 (dist. q, 1H, J=2.1 Hz).

MS-M+=373, 291, 289, 235, 127, 101, 85, 57, 43 (base).

EXAMPLE 19

N-(3-Tri-n-butylstannyl)cyclopent-2-enyl phthalimide (24)

A solution of diethyl azodicarboxylate (1.06 g, 6.1 mmol) in dry tetrahydrofuran (10 ml) was added dropwise to a stirred suspension of alcohol (23) (1.90 g, 5.1 mmol), phthalimide (0.90 g, 6.1 mmol), and triphenylphosphine (1.60 g, 6.1 mmol) in anhydrous tetrahydrofuran (15 ml). The resulting orange solution was stirred at room temperature under nitrogen for 24 hours. The solvent was then removed under reduced pressure, and the residue chromatographed on silica gel using hexane-ethyl acetate 10:1 as the eluent to afford 1.43 g (59%) of 3 as a light yellow oil.

IR (liquid film) - 719, 1106, 1389, 1714 cm$^{-1}$. $^1$H-NMR (CDCl$_3$) 0.77-1.14 (m, 15H), 1.15-1.77 (m, 12H), 2.00-2.45 (m, 2H), 2.47-2.75 (m, 1H), 2.76-2.97 (m, 1H), 5.36-5.45 (m, 1H), 5.65-5.69 (m, 1H), 7.66-7.71 (m, 2H), 7.75-7.83 (m, 2H).

MS-M+=502, 446, 380, 291, 266, 235 (base).

EXAMPLE 20

N-Tert-butoxycarbonyl-N-(3-tri-n-butylstannyl)cyclopent-2-enyl amide (25)

To a solution of phthalimide (24) (2.80 9, 5.6 mmol) in 95% ethanol (50 ml) was added hydrazine monohydrate (0.39 g, 7.8 mmol). The resulting solution was stirred at room temperature for 27 hours, during which time a white solid precipitated out of solution. The solvent was then evaporated under reduced pressure and the residue was suspended in methylene chloride (100 ml) and treated successively with triethylamine (2.3 ml, 16.7 mmol) and di-tert-butyl dicarbonate (2.62 g, 12.0 mmol). The resulting suspension was stirred at room temperature for 48 hours, and then concentrated under reduced pressure. The residue was taken up in methylene chloride and chromatographed on silica gel using hexane-ethyl acetate 10:1 as the eluent, to afford 1.90 g (72%) of 25 as a yellow oil.

IR (liquid film) - 1074, 1121, 1175, 1707 cm.$^{-1}$. $^{1}$H-NMR (CDCl$_3$) 0.80–0.95 (m, 21H), 1.20–1.39 (m, 6H), 1.45 (s, 9H), 2.19–2.62 (m, 4H), 4.37–4.55 (m, 1H), 4.59–4.80 (m, 1H), 5.70–5.82 (m, 1H).

MS (CI, CH$_4$) 474, 472 (M+), 446, 420, 416 (base), 291, 141.

EXAMPLE 21

1-Cyclopropyl-6-fluoro-1,4-dihydro-4-oxo-7-(3tert-butoxycarbonylaminocyclopent-1-enyl)-1:8-naphthyridine-3-carboxylic acid ethyl ester (26)

The reaction of chloronaphthyridine (16) (1.04 g, 3.3 mmol) and vinyl stannane 25 (1.89 g, 4.0 mmol) according to the procedure described for Example 13 afforded the title compound as a light tan solid.

$^{1}$H-NMR (CDCl$_3$) - 0.94–1.18 (m, 2H), 1.23–1.35 (m, 2H), 1.41 (t, 3H, J=7.1 Hz), 1.48 (s, 9H), 1.61–1.88 (m, 1H), 2.45–2.62 (m, 1H), 2.85–3.15 (m, 2H), 3.58–3.72 (m, 1H), 4.41 (q, 2H, J=7.1 Hz), 4.75–5.05 (m, 2H), 6.80–6.86 (br s, 1H), 8.36 (d, 1H, J=10.6 Hz), 8.70 (s, 1H).

MS (CI, CH$_4$) 458 (M+1), 361, 333, 277 (base).

EXAMPLE 22

1-Cyclopropyl-6-fluoro-1,4-dihydro-4-oxo-7-(3-aminocyclopent-1-enyl)-1,8-naphthyridine-3-carboxylic acid (27)

Compound 26 (160 mg, 0.35 mmol) was suspended in acetonitrile (10 ml) and treated with 5 N HCl (1 ml). The resulting solution was stirred at room temperature for 28 hours, during which time a white solid precipitated out. The solid was filtered, washed successively with cold acetonitrile and ether, and dried in vacuo, to give 20 mg of the title compound.

$^{1}$H-NMR (d$_6$-DMSO) - 1.09–1.27 (m, 4H), 1.83–1.98 (m, 1H), 2.40–2.58 (m, 1H), 2.90–3.02 (m, 1H), 3.30–3.50 (m, 1H), 3.80–3.90 (m, 1H), 4.50–4.60 (m, 1H), 6.88 (br s, 1H), 8.08–8.25 (m, 2H), 8.57 (d, 1H, J=10.5 Hz), 8.87 (s, 1H), 14.39–14.50 (br s, 1H). MS (EI) 329 (M ), 285, 270, 255, 84, 66 (base).

We claim:

1. A process for the preparation of a compound of formula

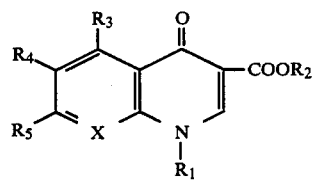

I or a pharmaceutically acceptable salt thereof wherein:
R$_1$ is lower alkyl,
aryl,
alkenyl,
cycloalkyl of from three to six carbon atoms,
R$_2$ is hydrogen, alkyl, or metal salts;
R$_3$ is hydrogen, halogen, OR$_8$, alkyl, N(R$_9$)$_2$
wherein R$_8$ is hydrogen, lower alkyl, lower acyl, trialkylsilyl
and R$_9$ is hydrogen, lower alkyl, lower acyl maleimido, phthalimido, succinimido;
R$_4$ is hydrogen, halogen or lower alkyl;
X is [N or ] CR$_{10}$ wherein R$_{10}$ is hydrogen, halogen, CN, CF$_3$, OR$_8$, alkyl, N(R$_9$)$_2$ wherein R$_8$ and R$_9$ are as above; [X and R$_1$ may be joined by C—Y—CH$_2$CH(CH$_3$) where Y is O, S or N-alkyl to form a ring;]
R$_5$ is [aryl,] [cycloalkyl,] [cycloalkenyl,]

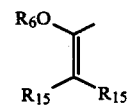

wherein R$_6$ is lower alkyl or R$_7$Si
wherein R$_7$ is lower alkyl or phenyl
and R$_{15}$ is hydrogen, alkyl, alkenyl, aryl, or halogen;
or
or R$_5$ may be a saturated or partially unsaturated heterocyclic ring

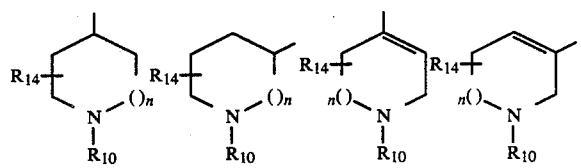

wherein n is an integer of from 0 to 4 and R$_{10}$ is hydrogen, lower alkyl, or lower acyl and R$_{14}$ is one or more substituents selected from H, alkyl, aryl, or halogen provided the ring is attached through a carbon atom of the heterocyclic ring,
or R$_5$ is

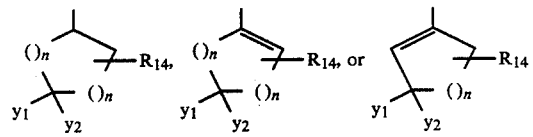

wherein Y$_1$ and Y$_2$ are each independently hydrogen, alkyl, OR$_8$, or N(R$_9$)$_2$ or taken together are =O or =NOR$_8$ wherein R$_8$ and R$_9$ are as above, and η=0–4 and R$_{14}$ is as above;
which comprises reacting a compound of formula

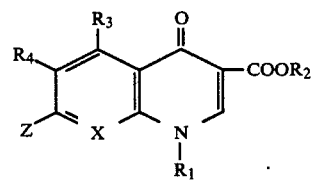

II or a pharmaceutically acceptable salt thereof wherein R$_1$, R$_2$, R$_3$, R$_4$, and X are as described above and [Z is halogen when the compound is a naphthyridine and] Z is (halogen)₃CSO₃-with a tetraorganostannane of the formula III (R₁₂)₃SnR₁₃ wherein R₁₂ is alkyl, [alkenyl, alkynyl, cycloalkyl, cycloalkenyl, or aryl] and R₁₃ is

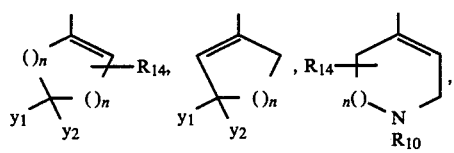

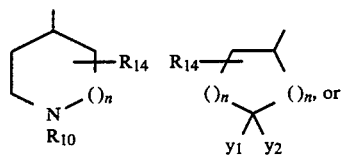

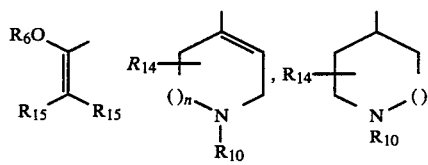

wherein n, R₁₄, R₁₀, R₆, R₁₅, Y₂ and Y₂ are as described previously in the claim to produce the desired compound of formula I.

2. A process according to claim 1 wherein R₅ is

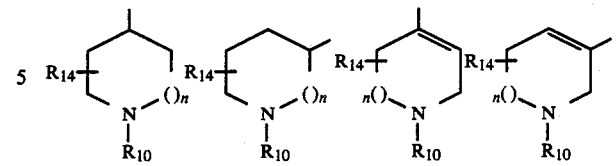

wherein n is an integer of from 0 to 4 and is as described above;
R₁₀ is hydrogen or lower alkyl and R₁₄ is more or more hydrogen or lower alkyl or R₅ is

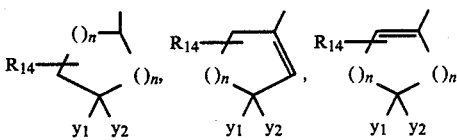

Y₁, Y₂ are independently hydrogen, alkyl, OR₈, N(R₉)₂ wherein R₈, R₁₄, and R₉ are as above and η=0–4 and is as described above.

3. A process according to claim 1 wherein the reaction takes place in a solvent selected from the group consisting of ether, tetrahydrofuran, 1,2-dialkoxyethane, dimethylformamide, DMA, and dioxane.

4. A process according to claim 3 wherein the solvent is selected from the group consisting of tetrahydrofuran, dimethylformamide, and dioxane.

5. A process according to claim 1 wherein the reaction is catalyzed by bis(triphenylphosphine)palladium (II) chloride, tetrakis(triphenylphosphine)palladium(0).

6. A process according to claim 1 wherein anhydrous lithium chloride is added to the reaction vessel.

7. A process according to claim 1 wherein an antioxidant is added to the reaction.

8. A process according to claim 7 wherein the antioxidant is selected from the group consisting of butylated hydroxy toluene and 2,6-ditertbutyl4-methylphenol.

9. A process according to claim 1 wherein the reaction temperature is from about 30° to about 200° C.

10. A process according to claim 1 wherein 60°–105° C.

* * * * *

UNITED STATES PATENT AND TRADEMARK OFFICE
CERTIFICATE OF CORRECTION

PATENT NO. : 4,945,160

DATED : July 31, 1990

INVENTOR(S) : John S. Kiely et al.

It is certified that error appears in the above—identified patent and that said Letters Patent is hereby corrected as shown below:

Column 24, line 11, delete "[N or]".

Column 24, lines 13-15, delete "[X and $R_1$ may be joined by $C-Y-CH_2CH(CH_3)$ where Y is O, S or N-alkyl to form a ring;]".

Column 24, line 16, delete "[aryl,] [cycloalkyl,] [cycloalkenyl,]".

Column 25, lines 1 and 2, delete "[Z is halogen when the compound is a naphthyridine and]".

Column 25, lines 4-5, delete "[alkenyl, alkynyl, cycloalkyl, cycloalkenyl, or aryl]".

Signed and Sealed this

Twenty-second Day of December, 1992

*Attest:*

DOUGLAS B. COMER

*Attesting Officer*  *Acting Commissioner of Patents and Trademarks*